United States Patent
Christian et al.

(10) Patent No.: US 10,335,237 B2
(45) Date of Patent: Jul. 2, 2019

(54) VISUAL ORIENTATION AID FOR MEDICAL INSTRUMENTS

(75) Inventors: Georg Christian, Munich (DE); Christian Maier, Munich (DE); Christian Lechner, Jesenwang (DE)

(73) Assignee: Brainlab AG, Munich (DE)

( * ) Notice: Subject to any disclaimer, the term of this patent is extended or adjusted under 35 U.S.C. 154(b) by 1836 days.

(21) Appl. No.: 12/412,398

(22) Filed: Mar. 27, 2009

(65) Prior Publication Data

US 2009/0254098 A1 Oct. 8, 2009

Related U.S. Application Data

(60) Provisional application No. 61/043,174, filed on Apr. 8, 2008.

(30) Foreign Application Priority Data

Apr. 3, 2008 (EP) .................................. 08154024

(51) Int. Cl.
| | | |
|---|---|---|
| A61B 17/00 | (2006.01) | |
| A61B 34/10 | (2016.01) | |
| A61B 17/17 | (2006.01) | |
| A61B 34/20 | (2016.01) | |

(52) U.S. Cl.
CPC .............. *A61B 34/10* (2016.02); *A61B 17/17* (2013.01); *A61B 17/1721* (2013.01); *A61B 2034/102* (2016.02); *A61B 2034/107* (2016.02); *A61B 2034/2068* (2016.02)

(58) Field of Classification Search
USPC ......... 606/130; 600/424, 425, 426, 427, 431
See application file for complete search history.

(56) References Cited

U.S. PATENT DOCUMENTS

| | | |
|---|---|---|
| 5,186,418 A | 2/1993 | Lauritsen |
| 5,585,726 A | 12/1996 | Chau |
| 5,921,992 A | 7/1999 | Costales et al. |
| 6,021,343 A | 2/2000 | Foley et al. |
| 6,144,899 A | 11/2000 | Babb et al. |
| 6,236,875 B1 | 5/2001 | Bucholz et al. |
| 6,379,302 B1 | 4/2002 | Kessman et al. |
| 6,484,049 B1 | 11/2002 | Seeley et al. |
| 6,490,467 B1 | 12/2002 | Bucholz et al. |
| 6,490,475 B1 | 12/2002 | Rossi et al. |
| 6,535,756 B1 | 3/2003 | Simon et al. |

(Continued)

FOREIGN PATENT DOCUMENTS

| | | |
|---|---|---|
| EP | 1 002 502 | 5/2000 |
| EP | 1 491 150 | 12/2004 |

(Continued)

*Primary Examiner* — Patricia J Park
(74) *Attorney, Agent, or Firm* — Tucker Ellis, LLP

(57) ABSTRACT

The invention relates to a method for visually assisting the alignment of a medical instrument, wherein the instrument is visually displayed on an image output in a positional relationship to a part of a patient's body by means of a medical navigation system, wherein an orientation aid is displayed as a virtual model shape at the instrument or in a particular positioning with respect to a characteristic part of the instrument. It also relates to a planning method for optimized instrument alignment with the aid of such an image assisting method.

9 Claims, 4 Drawing Sheets

(56) References Cited

U.S. PATENT DOCUMENTS

| | | |
|---|---|---|
| 6,669,635 B2 | 12/2003 | Kessman et al. |
| 6,725,080 B2 | 4/2004 | Melkent et al. |
| 6,920,347 B2 | 7/2005 | Simon et al. |
| 6,920,390 B2 | 7/2005 | Mallet et al. |
| 6,921,051 B2 | 7/2005 | Lopata et al. |
| 6,968,224 B2 | 11/2005 | Kessman et al. |
| 7,103,368 B2 | 9/2006 | Teshma |
| 7,139,601 B2 | 11/2006 | Bucholz et al. |
| 7,204,840 B2 | 4/2007 | Skakoon et al. |
| 7,606,613 B2 * | 10/2009 | Simon et al. ............... 600/426 |
| 2001/0034530 A1 | 10/2001 | Malackowski et al. |
| 2003/0073901 A1 * | 4/2003 | Simon et al. ............... 600/424 |
| 2003/0120283 A1 * | 6/2003 | Stoianovici ............ A61B 34/70 606/130 |
| 2004/0082849 A1 * | 4/2004 | Schweikard ............ G06T 15/20 600/424 |
| 2004/0087852 A1 * | 5/2004 | Chen et al. ............... 600/407 |
| 2005/0085717 A1 * | 4/2005 | Shahidi ..................... 600/424 |
| 2005/0267360 A1 | 12/2005 | Birkenbach et al. |
| 2006/0025679 A1 * | 2/2006 | Viswanathan ......... A61B 6/548 600/424 |
| 2007/0038059 A1 * | 2/2007 | Sheffer et al. ............... 600/407 |
| 2008/0004633 A1 * | 1/2008 | Arata ..................... A61B 34/20 606/130 |
| 2008/0234575 A1 * | 9/2008 | Klingenbeck-Regn et al. ............ 600/431 |

FOREIGN PATENT DOCUMENTS

| | | |
|---|---|---|
| WO | 00/64367 | 11/2000 |
| WO | 02/009611 | 2/2002 |

* cited by examiner $$\delta^* - \delta = 2\arctan\left\{\frac{1-\cos\alpha}{\tan(\delta/2) + [\cos\alpha / \tan(\delta/2)]}\right\}$$

VISUAL ORIENTATION AID FOR MEDICAL INSTRUMENTS

RELATED APPLICATION DATA

This application claims the priority of U.S. Provisional Application No. 61/043,174, filed on Apr. 8, 2008, which is hereby incorporated in its entirety by reference.

FIELD OF THE INVENTION

The invention relates to a visual orientation aid for medical instruments or, in other words, to a method for visually assisting the alignment of a medical instrument.

BACKGROUND OF THE INVENTION

Medical navigation allows medical instruments to be located and positionally traced (tracking) with the aid of a tracking and navigation system. The instruments shown can then be displayed on an image output (for example, a screen) in their correct or current positional relationship to a patient's body or parts of a patient's body, if the patient has been scanned by means of an imaging method (CT, MR, etc.) and registered in the navigation system beforehand. Within this setting, the present invention is intended to provide visual assistance in aligning and/or orienting instruments.

It is often necessary to exactly align instruments or to exactly plan their alignment, for example when implants have to be exactly placed at particular bone structure positions. The position of an implant is then for example set by a surgeon by considering adjacent anatomical landmarks, unique bone structures or pre-planned points and axes. When fixing a pelvic fracture, for example, the trajectory of the inserted screw has to have a specific angle to the lateral proximal femoral bone surface, i.e. usually about 130°. In order to set a suitable placement of the pelvic screw, a special drill guide is usually used which is pressed on the lateral cortex of the greater trochanter region. The guide hole of the drill guide is aligned such that its axis points to the femoral neck at an angle of 130° to the proximal femoral bone axis.

In this example, but also in other surgeries, a separate and dedicated tool is therefore required in order to be able to correctly insert a medical instrument. This special tool often also requires contact with bone structures or other body structures which are not normally exposed, such that an extensive and invasive preparation—i.e. opening up the patient—is often necessary.

The same problem also for example occurs when the entry point for specific implants has to be prepared, such as for example a lateral femoral nail, wherein a specific point on the lateral proximal femur has to be found by attaching a template. In this case, too, highly invasive preparations in the bone region are necessary.

SUMMARY OF THE INVENTION

It is the object of the present invention to provide a method for visually assisting the alignment of a medical instrument, which makes the use of special alignment tools unnecessary. The intention is in particular also to reduce as significantly as possible the invasiveness of preparations for the alignment of instruments; specifically, the intention is to be able to omit, as completely as possible, invasive techniques for instrument alignment only.

This object is solved in accordance with the invention by a method in which the instrument is visually displayed on an image output in a positional relationship to a part of a patient's body by means of a medical navigation system, wherein an orientation aid is displayed as a virtual model shape at the instrument or in a particular positioning with respect to a characteristic part of the instrument (a part on the instrument or a geometric characteristic, for example an axis, surface, etc.). The sub-claims define preferred embodiments of the invention.

In other words, the invention comprises displaying a specific shape relative to a specific part of an instrument, on an image data set which is used with a medical navigation system, i.e. an orientation aid which is related both to the instrument being used and to the part of the patient's body being treated or its environment is superimposed onto the image data material, together with the representation of the instrument, and on the basis of this superimposition, it is then possible for the user to assess whether the instrument is correctly or incorrectly aligned. A hardware, i.e. a separate alignment tool, is no longer required and can accordingly be omitted. Invasive steps for attaching this hardware (for example, to a bone) also become superfluous and no longer have to be performed.

In one embodiment of the invention, specific geometric characteristics such as axes or planes or landmarks and/or landmark-like portions of the part of the patient's body are visually displayed as auxiliary representations, with respect to which the virtual model shape can be and/or is aligned. The model shape can also be adapted to the part of the patient's body or to a characteristic portion of it, or to the aforementioned specific geometric characteristic or one of the aforementioned specific geometric characteristics. If, for example, a particular axis (for example, a bone axis) is displayed with respect to the part of the patient's body, it is advantageous if the superimposed model also has an exterior shape which can be placed onto said axis or attached so as to correspond to it, i.e. the model shape should have a linear exterior boundary which can then be placed onto the axis or superimposed onto it.

It is possible to alter, adapt or exchange the model shape using settings on the navigation system and/or to make a selection from a number of model shapes if the invention is implemented in accordance with a preferred embodiment.

In a specific configuration of the method in accordance with the invention, the model shape assists an angular orientation of the instrument with respect to the part of the patient's body; in particular, the model shape displays an angular range about an axis of the instrument. In one variant, this can be solved such that the model shape is a conical shape which is aligned with respect to the axis of the instrument, in particular with the tip of the cone at the tip of the instrument.

The model shape can however also assume other forms. It can be a representation of an operation aid, specifically an implant, a plate, a template or a guide, or a virtual representation of a part of a patient's body in a desired positional assignment to the instrument. In the latter case in which the model shape is a virtual representation of the part of the patient's body with respect to which the instrument is to be aligned, a correspondence between the virtual representation of the body part and the body part (from the patient image data) will indicate a desired positioning of the instrument. In other words, a sort of "silhouette" of the part of the patient's body (can) also be superimposed onto the representation of the patient data set, together with the instrument. The instrument can then be moved until the superimposed (virtual) silhouette lies over the corresponding displayed portion from the patient data set; the positioning of the instrument is then correct.

The model shape can be introduced into the image output as a projection, and it is then advantageous if the model shape is projected, in an adapted form, onto the image plane of the representation of the part of the patient's body and visually displayed in this way in the projection. One example would be: a particular angle will be increased or reduced depending on the alignment of the instrument, if the instrument is held in different placements with respect to the image plane. It therefore depends on whether the representation of the virtual angle on the image plane of the patient data corresponds, and it is therefore advantageous to project the model shape onto this image plane depending on the position.

In accordance with another aspect, the invention also relates to a method for planning an optimized instrument alignment with the aid of an image assisting method such as is described here in the many different embodiment variants.

Put slightly differently, the invention and/or its embodiments can be defined such that they comprise displaying a specific shape on an instrument, for example a conical shape—having a particular aperture angle at the tip of the representation of a surgical instrument—on an image data set which is used in a medical navigation system. The aperture angle of the cone can be set in the navigation software application, and the cone is intended to serve as a visual aid, in order to align its circumferential line with a given axis, thus creating half an aperture angle between the axis of the instrument and the predetermined axis. The aperture angle of the cone can be freely set, such that the invention can be used for different indications. The invention also allows the positioning of the implant to be planned without physical contact between any template and the surface of the bone. In the same way, any shape could be projected at the instrument or tip of the instrument, in order to assist the exact planning of the position of the implant without invasively penetrating onto the bone with any templates.

The invention can for example be used wherever a trajectory of a screw or wire or other predefined shape has to be aligned in a (drill) guide relative to a predetermined axis or shape which for example is predetermined by a bone in a registered image. In the example with the cone, the desired angle between the trajectory of the screw and a predetermined axis can be freely set within the maximum possible range of 0° to 180°, and this setting changes the aperture angle of the cone which is imaged at the tip of the representation of the medical and/or surgical instrument. Matching the circumferential line (enveloping end) of the cone to the predetermined surface of the bone ensures that the axis of the instrument (drill guide or screwdriver) lies at the selected angle to the predetermined axis or surface.

BRIEF DESCRIPTION OF THE DRAWINGS

The invention is illustrated below in more detail on the basis of the enclosed drawings and example embodiments. It can include any of the features described here, individually and in any expedient combination.

DETAILED DESCRIPTION

Figure 1:
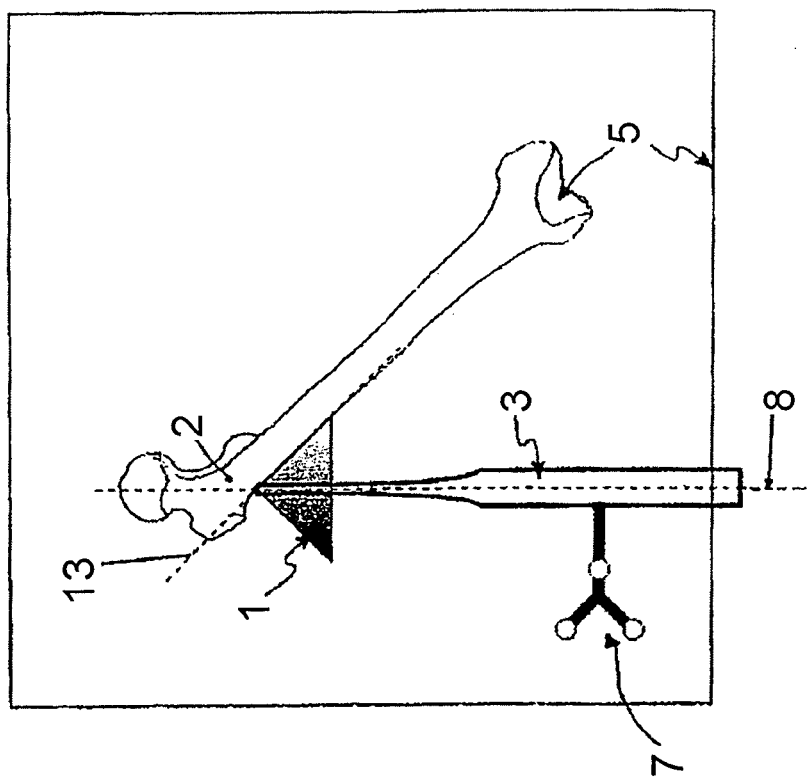
FIG. 1 shows a schematic representation of a navigation system and an image assistance in accordance with the invention.
Figure 1:
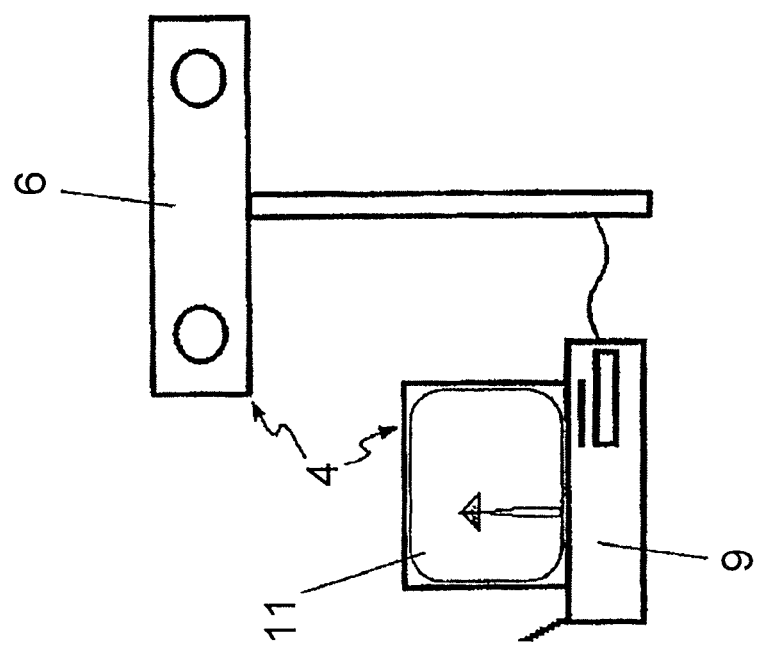

A medical tracking and navigation system, which bears the reference sign 4 as a whole, is shown on the left in FIG. 1. It consists of a tracking unit 6 comprising cameras, a computer unit 9 and a screen 11 (the image output). An instrument 3, shown on the right, is tracked—i.e. located and traced—using the tracking unit 6, via the reference array 7 which is attached to the instrument 3. The instrument has the axis 8.

The instrument 3 is tracked and displayed in its correct positional relationship, in relation to a registered patient data set which is obtained for example by a CT or MR scanner recording. In this case, the image data set bears the reference sign 5 and in particular comprises the image plane and the representation of a femoral bone 2.

A cone 1 having a certain aperture angle is superimposed onto the image output at the tip of the instrument 3, and in this case, said cone 1 forms a virtual model shape. When the exterior enveloping straight line of the cone 1 lies on the plane which is indicated in FIG. 1 by the reference sign 13, the instrument is correctly aligned, i.e. the axis 8 of the instrument points in the correct direction, in order for example to produce a drill hole or to insert a bone wire. It becomes clear in the representation that the axis 8 then passes through the femoral neck exactly as desired. The cone 1, which abuts the line 13—which reflects a predetermined plane—when the instrument is correctly aligned, thus replaces the attachment of a drilling template to the bone 3 in this case, and so avoids the corresponding invasive preparation.

Figure 2:
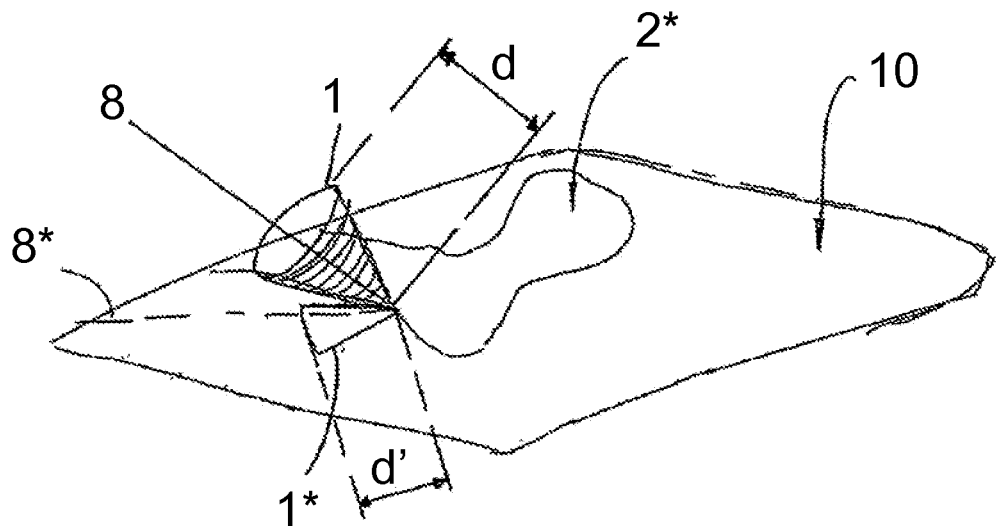
FIGS. 2 and 3 show representations for projecting a model shape onto an image plane.
Figure 3:
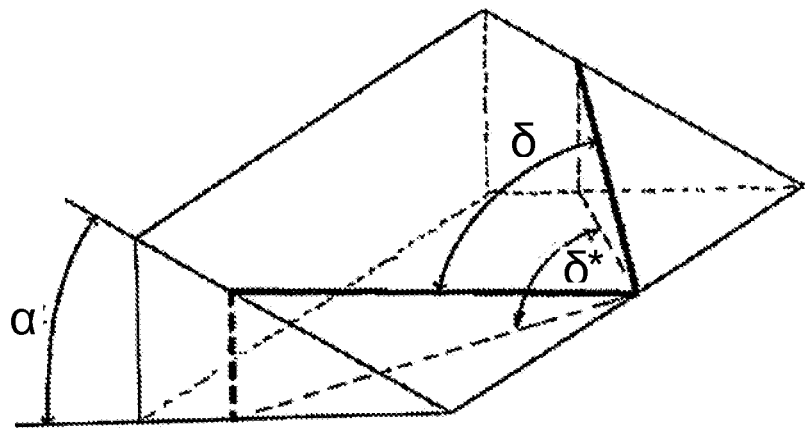

Because the instrument is separately tracked and will have a certain angular relationship to the image plane in which the patient data set is displayed, this angular placement has to be considered when displaying the model shape, i.e. in this case, the cone 1. This is achieved by a projection onto the image plane, as shown in FIGS. 2 and 3. The cone 1 around the axis 8 of the instrument (each in a 3D representation) is imaged in the image plane 10 in which the bone representation 2* also lies, thus creating the representation 8* of the axis and the representation 1* of the cone, which in this representation will have a different aperture angle to that previously input and predetermined in the navigation system. The cone length will also be shortened in the projection (d'<d). Due to the projection, however, the cone can be correctly re-attached to the auxiliary line (the enveloping end of the cone on the line 13 in FIG. 1) and optically monitored. FIG. 3 shows how a change in angle $\delta^*-\delta$ then occurs, given a tilt by the angle $\alpha$, wherein the change in angle then reflects the altered projected angle. FIG. 3 also specifies the mathematical relationship for the change in angle, which can be used by the navigation system when projecting in the image material.

Figure 4:
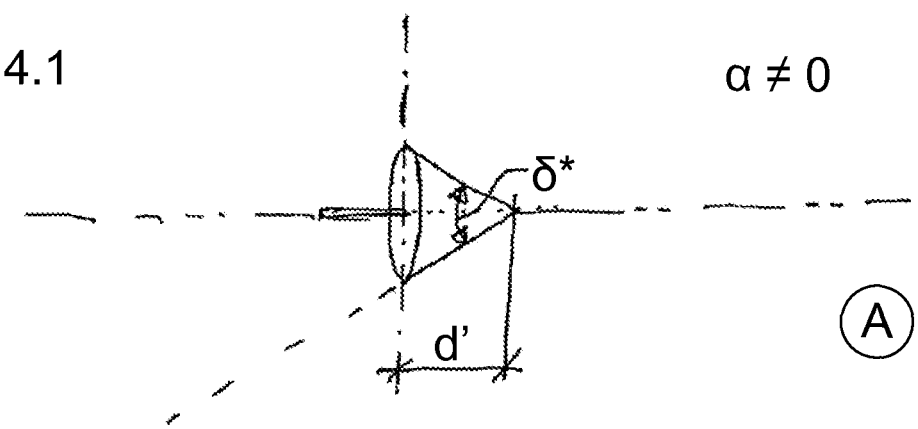
FIG. 4 shows four different representations for projecting a cone.
Figure 4:
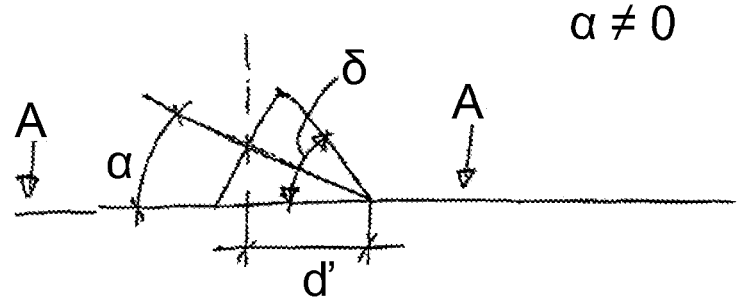
Figure 4:
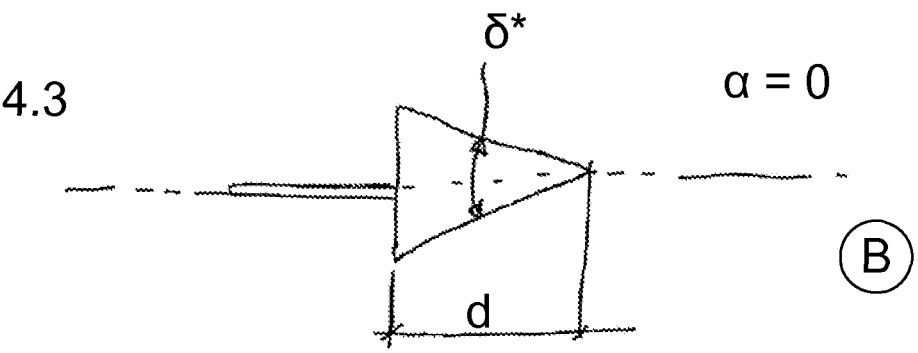
Figure 4:
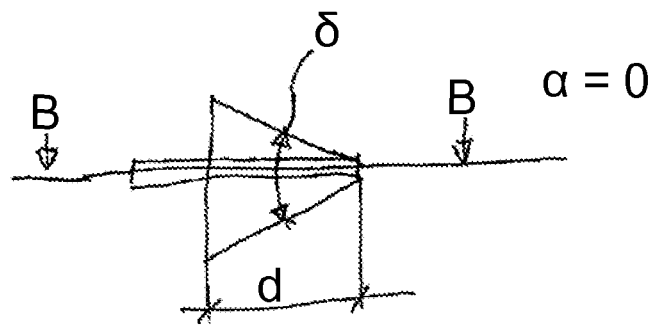

FIG. 4 shows again, somewhat more exactly in individual representations, the imaging relationships for instruments which are inclined with respect to the image plane (4.1 and 4.2) and for an instrument in the image plane (4.3 and 4.4). A cone which is arranged at an inclination with respect to the image plane is schematically shown in the two individual representations 4.1 and 4.2, wherein the individual representation 4.1 shows a view from above onto the image plane A, and the individual representation 4.2 shows a view parallel to the image plane A. It will be seen that in the view 4.1, the imaged conical angle (angle of the cone) δ* is slightly smaller than the actual aperture angle δ of the cone which can be seen, undistorted, in the representation 4.2. The representation of the cone is also shortened as a whole, since it assumes the length d' when an obliquely held instrument ($\alpha \neq 0$) is imaged. This follows in particular from a comparison with the representations 4.3 and 4.4, which show the scenario in which the axis of the instrument and therefore also the axis of the cone lies in the image plane B. The elevation angle a to the image plane therefore becomes zero, and no distortions in the projection are created, i.e. the aperture angle δ corresponds to the projected aperture angle δ*, and the length d of the cone is also correctly imaged; d' is thus smaller than d for the same cone. In the representations 4.3 and 4.4, it is also the case that 4.3 shows a view from above onto the plane B and 4.4 shows a view parallel to the plane B.

Figure 5:
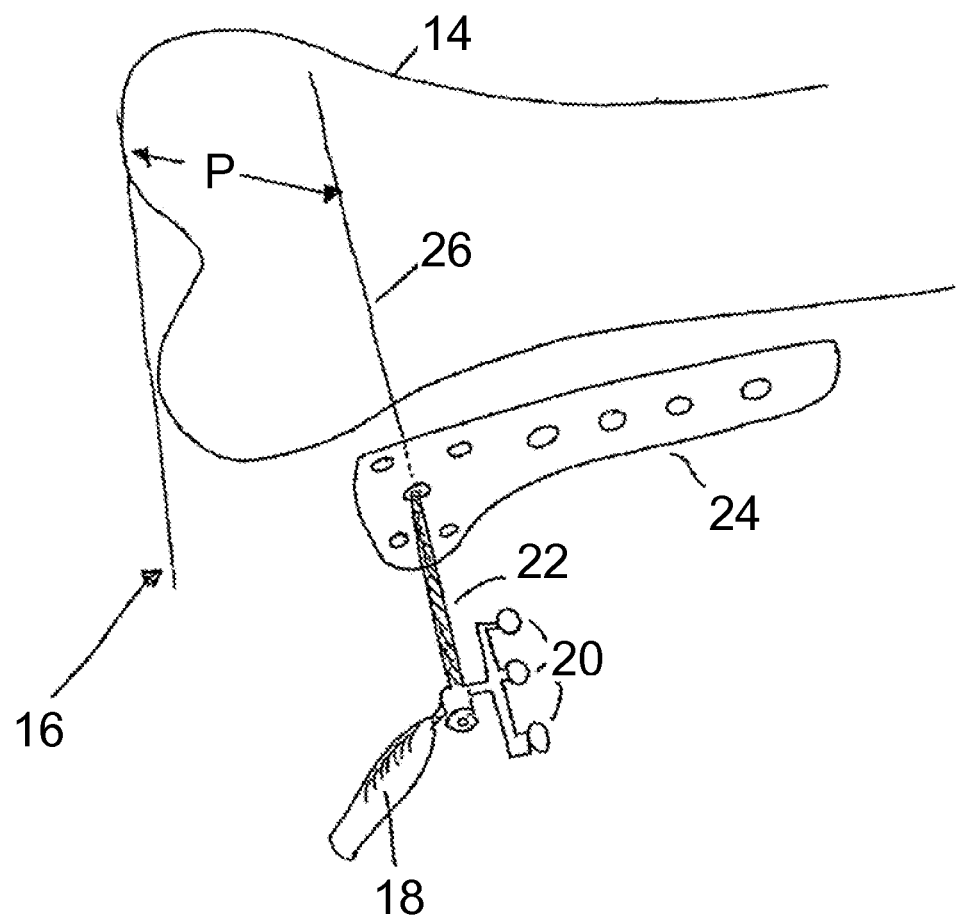
FIG. 5 shows a schematic representation for virtually superimposing an implant plate.

FIG. 5 is intended to also show that it is not only geometric elements such as for example the cone 1 which can be virtually displayed as a model shape. Rather, virtual representations of operation aids—for example, implants, screws, etc.—are also suitable for being virtually displayed in the navigation assistance. FIG. 5 shows such a plate 24. Pre-digitized versions of such plates or other surgical aids are often already available because they are often already provided in a uniform size or in different sizes and made navigable as templates. It is thus for example possible to track the instrument 18—in this case, a drill guide—using the marker array 20, such that the axis 26 of the sleeve 22 can be shown as a superimposition on the patient data set, which in this case shows the head 14 of a bone (the distal femur). The template 24 for a plate, which is to be fixedly drilled through a particular hole at a particular angle, is then additionally superimposed as a model shape. The arrangement of the plate can be determined by the arrangement of the hole with respect to the sleeve (drill guide) 22, and the drilling direction can be determined by the arrangement of the axis 26 parallel to the distal knee joint axis, which in this case is schematically indicated by 16. The two auxiliary lines 16 and 26 (the axis) run in parallel, as is intended to be indicated by the letter P.

Thus, a plate 24 can therefore also for example be navigated as a model shape, and the alignment of the instrument 18 comprising the drill sleeve 22 (drill guide) can be planned with visual assistance.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method comprising:
    displaying, on an image output of a medical navigation system, a virtual representation of a medical instrument in a positional relationship to a part of a patient's body, the virtual representation of the medical instrument having an axis and a tip; and
    displaying, on the image output of the medical navigation system, an orientation aid situated at the tip of the virtual representation of the medical instrument, the orientation aid shaped as a cone having a symmetry axis coinciding with the axis of the visual representation of the medical instrument and a particular aperture angle based on a desired orientation of the medical instrument relative to a predefined axis of the part of the patient's body, the particular aperture angle of the cone determining an exterior enveloping straight line of the cone, the exterior enveloping straight line of the cone abutting the predefined axis of the part of the patient's body indicating that the medical instrument has the desired orientation.

2. The method according to claim 1, wherein axes or planes or landmarks and/or landmark-like portions of the part of the patient's body are visually displayed as auxiliary representations, with respect to which the virtual representation of the medical instrument and orientation aid can be and/or is aligned.

3. The method according to claim 1, wherein the virtual representation of the medical instrument can be altered, adapted or exchanged using settings on the navigation system and/or can be selected from a number of models.

4. The method according to claim 1, wherein the virtual representation of the medical instrument is a virtual representation of an operation aid.

5. The method according to claim 4, wherein the operation aid is an implant, a plate, a template or a guide.

6. The method according to claim 1, wherein the virtual representation of the medical instrument and the orientation aid are introduced into the image output of the medical navigation system as a projection.

7. The method according to claim 6, wherein the virtual representation of the medical instrument and the orientation aid are projected, in an adapted form, onto the image plane of the representation of the part of the patient's body and visually displayed in the projection.

8. A method for planning an optimized instrument alignment using the image assisting method in accordance with claim 1, the method comprising:
   using the virtual representation of the medical instrument and the orientation aid to serve as aids in aligning the medical instrument for use during a medical procedure.

9. A non-transitory computer readable storage medium storing a computer program which, when running on a computer or loaded onto the computer, causes the computer to:
   display, on an image output of an associated medical navigation system, a virtual representation of a medical instrument on an image output in a positional relationship to a part of a patient's body, the virtual representation of the medical instrument having an axis and a tip; and
   display, on the image output of the associated medical navigation system, an orientation aid situated at the tip of the virtual representation of the medical instrument, the orientation aid shaped as a cone having a symmetry axis coinciding with the axis of the visual representation of the medical instrument and a particular aperture angle based on a desired orientation of the medical instrument relative to a predefined axis of the part of the patient's body, the particular aperture angle of the cone determining an exterior enveloping straight line of the cone, the exterior enveloping straight line of the cone abutting the predefined axis of the part of the patient's body indicating that the medical instrument has the desired orientation.

* * * * *